US011998771B2

(12) United States Patent
Jancarik et al.

(10) Patent No.: US 11,998,771 B2
(45) Date of Patent: Jun. 4, 2024

(54) COMPACT RESPIRATOR ASSEMBLY

(71) Applicant: Honeywell International Inc., Charlotte, NC (US)

(72) Inventors: Julius Jancarik, Drasov (CZ); Garaga Phani Kumar, Hyderabad (IN); Rahul Ramesh Bhaskarwar, Hyderabad (IN)

(73) Assignee: Honeywell International Inc., Charlotte, NC (US)

(*) Notice: Subject to any disclaimer, the term of this patent is extended or adjusted under 35 U.S.C. 154(b) by 424 days.

(21) Appl. No.: 17/330,063

(22) Filed: May 25, 2021

(65) Prior Publication Data
US 2021/0369996 A1 Dec. 2, 2021

(30) Foreign Application Priority Data
May 27, 2020 (IN) .............................. 202011022172

(51) Int. Cl.
A62B 18/00 (2006.01)
A61M 16/00 (2006.01)
(Continued)

(52) U.S. Cl.
CPC ....... A62B 18/006 (2013.01); A61M 16/0051 (2013.01); A61M 16/0066 (2013.01);
(Continued)

(58) Field of Classification Search
CPC .......... A61M 16/0051; A61M 16/0066; A61M 16/105; A61M 2205/18; A61M 2205/50;
(Continued)

(56) References Cited

U.S. PATENT DOCUMENTS 8,667,959 B2  3/2014 Tilley et al.
9,481,424 B2  11/2016 Hagen et al.
(Continued)

FOREIGN PATENT DOCUMENTS

EP  0241188 A1 * 10/1987 ........... A62B 18/006
EP  0241188 A1  10/1987
(Continued)

OTHER PUBLICATIONS

Extended European Search Report issued in European Application No. 21176368.5 dated Sep. 30, 2021, 10 pages.
(Continued)

Primary Examiner — Joseph D. Boecker
(74) Attorney, Agent, or Firm — Alston & Bird LLP

(57) ABSTRACT

Various embodiments are directed to a compact respirator assembly comprising a respirator housing; and a compact blower assembly, the compact blower assembly comprising an impeller configured to pull a volume of air into a blower assembly air inlet; a blower scroll configured to receive the volume of air and direct the volume of air toward a blower scroll air outlet, the blower scroll comprising: a first blower scroll component comprising at least a portion of a blower frame element comprising a portion of the respirator housing; a second blower scroll component comprising a scroll cover secured to the blower frame element so as to define an internal scroll flow chamber, wherein the internal scroll flow chamber comprises a cavity positioned between the scroll cover and the blower frame element; and wherein the blower scroll air inlet comprises an opening that extends through a thickness of the respirator housing.

18 Claims, 7 Drawing Sheets

(51) Int. Cl.
*A61M 16/10* (2006.01)
*F04D 29/42* (2006.01)

(52) U.S. Cl.
CPC ....... *A61M 16/105* (2013.01); *F04D 29/4226* (2013.01); *A61M 2205/18* (2013.01); *A61M 2205/3365* (2013.01); *A61M 2205/50* (2013.01); *A61M 2205/581* (2013.01)

(58) Field of Classification Search
CPC ........... A61M 2205/581; A62B 18/006; A62B 18/045; F04D 29/4226; A42B 3/286
See application file for complete search history.

(56) References Cited

U.S. PATENT DOCUMENTS

| | | | |
|---|---|---|---|
| 2006/0048782 A1 | 3/2006 | Gossweiler | |
| 2010/0224190 A1* | 9/2010 | Tilley | A62B 18/006 128/205.12 |
| 2011/0240026 A1 | 10/2011 | Ausen | |
| 2012/0051904 A1* | 3/2012 | Hagen | B62K 11/02 415/224 |
| 2012/0199129 A1* | 8/2012 | Kenyon | F04D 17/16 128/205.25 |

FOREIGN PATENT DOCUMENTS

| | | |
|---|---|---|
| EP | 3402991 B1 | 10/2019 |
| WO | 2017/151085 A1 | 9/2017 |

OTHER PUBLICATIONS

EP Office Action Mailed on Mar. 1, 2024 for EP Application No. 21176368, 4 page(s).

* cited by examiner

COMPACT RESPIRATOR ASSEMBLY

CROSS-REFERENCE TO RELATED APPLICATIONS

This patent application claims priority to Indian Patent Application Ser. No. 202011022172, filed May 27, 2020 and entitled "A Compact Respirator Assembly," which is incorporated herein by reference.

FIELD OF THE INVENTION

Various embodiments described herein relate generally to a compact respirator apparatus. In particular, various embodiments are directed to respirators comprising a compact blower assembly configured for delivering a volume of breathable air to a user.

BACKGROUND

Industrial and commercial applications may use respirators comprising blowers to provide a powered flow of air. Through applied effort, ingenuity, and innovation, Applicant has solved problems relating to blower apparatuses by developing solutions embodied in the present disclosure, which are described in detail below.

BRIEF SUMMARY

Various embodiments are directed to a compact respirator assembly and method of using the same. In various embodiments, a respirator apparatus may comprise a respirator housing comprising an outer casing defining an exterior portion of the respirator apparatus; and a compact blower assembly comprising: an impeller configured to pull a volume of air into the blower assembly through a blower assembly air inlet; a blower scroll configured to receive the volume of air at a blower scroll air inlet and direct the volume of air toward a blower scroll air outlet, the blower scroll comprising: a first blower scroll component comprising at least a portion of a blower frame element and defining the blower scroll air inlet, wherein the blower frame element comprises a portion of the respirator housing; and a second blower scroll component comprising a scroll cover secured to the blower frame element so as to define an internal scroll flow chamber, wherein the internal scroll flow chamber comprises comprising a cavity positioned between the scroll cover and the portion of the blower frame element corresponding to the first blower scroll component; and wherein the blower scroll is configured to house the impeller within the internal scroll flow chamber; wherein the blower scroll air inlet comprises an opening extending through a thickness of the blower frame element, wherein the blower assembly is configured such that the blower scroll air inlet embodies the blower assembly air inlet.

In various embodiments, the thickness of the blower frame element may extend between a first blower frame element surface and a second blower frame element surface, wherein the first blower frame element surface is configured to receive an interface portion of the scroll cover such that the scroll cover may be secured thereto, wherein the internal scroll flow chamber is defined between the scroll cover and the first blower frame element surface. In certain embodiments, the first blower frame element surface may comprise one or more geometric features configured to facilitate an airflow of the volume of air from the blower scroll air inlet to the blower scroll air outlet within the internal scroll flow chamber. In certain embodiments, the impeller is secured to the first blower frame element surface.

In various embodiments the scroll cover may comprise an interface surface configured to engage a first blower frame element surface so as to define an interface between the first blower scroll component and the second blower scroll component, the interface surface having a substantially annular configuration defined in part by an outer perimeter of the scroll cover, wherein the interface between the first blower scroll component and the second blower scroll component comprises an interface perimeter corresponding to the interface surface of the scroll cover. In certain embodiments, the blower scroll may be configured such that the interface perimeter extends along the first blower frame element surface so as to at least substantially surround the blower scroll air inlet. In various embodiments, the scroll cover may further comprise an external back surface having an at least substantially planar configuration, the external back surface defining a portion of an exterior of the scroll cover that is configured to engage at least a portion of the printed control board assembly.

In various embodiments, the respirator apparatus may further comprise a blower motor configured to drive a rotation of the impeller within the internal scroll flow chamber and a printed control board assembly, the printed control board assembly comprising: motor control circuitry configured to facilitate transmission of one or more signals to the blower motor; and respirator control circuitry configured to facilitate transmission of one or more signals to one or more respirator operational components. In various embodiments, the scroll cover further comprises a beeper interface element integrated into an exterior of the scroll cover and configured to be in electronic communication with the printed control board assembly and a beeper element so as to enable an alert functionality corresponding to one or more predetermined blower assembly operating parameters. In various embodiments, respirator apparatus may further comprise a filter assembly configured to at least partially purify the volume of air, wherein the filter assembly defines a portion of a respirator air flow path arranged upstream from the blower assembly. In certain embodiments, the respirator housing may comprise: an internal respirator housing portion defined at least in part by one or more sidewalls; and an external housing compartment disposed about an exterior of the respirator housing and defined at least in part by an outer surface of the blower frame element; wherein the blower assembly is disposed within the internal respirator housing portion and the filter assembly is disposed within the external housing compartment.

Various embodiments are directed to a compact blower assembly comprising: an impeller configured to pull a volume of air into the blower assembly through a blower assembly air inlet; a blower scroll configured to receive the volume of air at a blower scroll air inlet and direct the volume of air toward a blower scroll air outlet, the blower scroll comprising: a first blower scroll component comprising at least a portion of a blower frame element, wherein the blower frame element is configured so as to define at least a portion of an exterior of the blower assembly; a second blower scroll component comprising a scroll cover secured to the blower frame element so as to define an internal scroll flow chamber, wherein the internal scroll flow chamber comprises a cavity positioned between the scroll cover and the portion of the blower frame element corresponding to the first blower scroll component; and wherein the blower scroll is configured to house the impeller within the internal scroll flow chamber; wherein the blower scroll air inlet comprises an opening extending through a thickness of the blower frame element, wherein the blower assembly is configured such that the blower scroll air inlet embodies the blower assembly air inlet.

In various embodiments, the thickness of the blower frame element may extend between a first blower frame element surface and a second blower frame element surface, wherein the first blower frame element surface is configured to receive an interface portion of the scroll cover such that the scroll cover may be secured thereto, wherein the internal scroll flow chamber is defined between the scroll cover and the first blower frame element surface. In certain elements, the first blower frame element surface comprises one or more geometric features configured to facilitate an airflow of the volume of air from the blower scroll air inlet to the blower scroll air outlet within the internal scroll flow chamber. In certain embodiments, wherein the impeller may be secured to the first blower frame element surface. In various embodiments, the scroll cover may comprise an interface surface configured to engage a first blower frame element surface so as to define an interface between the first blower scroll component and the second blower scroll component, the interface surface having a substantially annular configuration defined in part by an outer perimeter of the scroll cover, wherein the interface between the first blower scroll component and the second blower scroll component comprises an interface perimeter corresponding to the interface surface of the scroll cover. In certain embodiments, the blower scroll is configured such that the interface perimeter extends along the first blower frame element surface so as to at least substantially surround the blower scroll air inlet.

In various embodiments, the scroll cover may further comprise an external back surface having an at least substantially planar configuration, the external back surface defining a portion of an exterior of the scroll cover that is configured to engage at least a portion of the printed control board assembly. In various embodiments, the compact blower assembly may further comprise a blower motor configured to drive a rotation of the impeller within the internal scroll flow chamber and printed control board assembly, the printed control board assembly comprising: motor control circuitry configured to facilitate transmission of one or more signals to the blower motor; and respirator control circuitry configured to facilitate transmission of one or more signals to one or more respirator operational components. In various embodiments, the scroll cover may further comprise a beeper interface element integrated into an exterior of the scroll cover and configured to be in electronic communication with the printed control board assembly and a beeper element so as to enable an alert functionality corresponding to one or more predetermined blower assembly operating parameters.

BRIEF DESCRIPTION OF THE DRAWINGS

Reference will now be made to the accompanying drawings, which are not necessarily drawn to scale, and wherein.

DETAILED DESCRIPTION

Figure 1A:
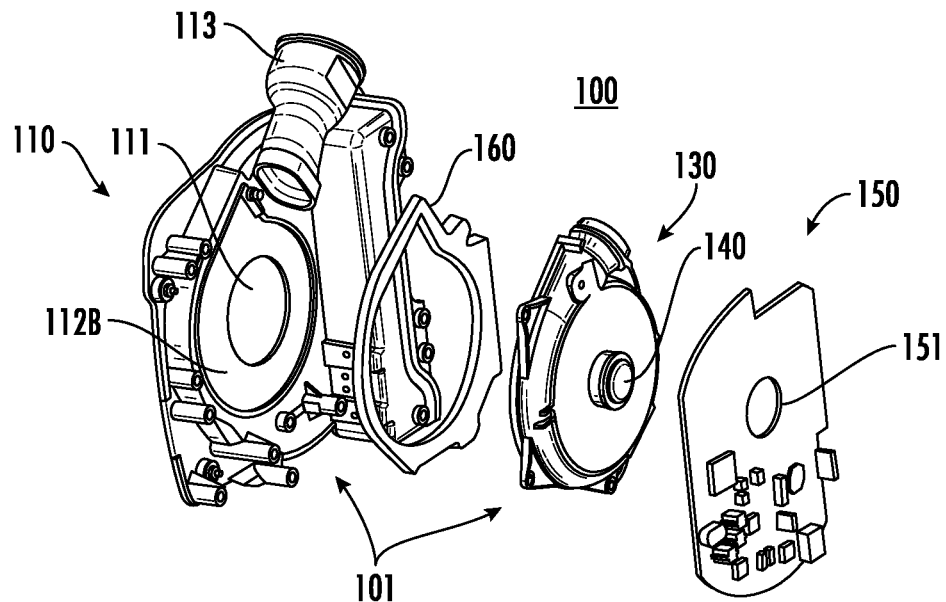
FIGS. 1A-1B illustrate exploded perspective views of various components of an exemplary blower apparatus in accordance with various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The words "example," or "exemplary," when used herein, are intended to mean "serving as an example, instance, or illustration." Any implementation described herein as an "example" or "exemplary embodiment" is not necessarily preferred or advantageous over other implementations.

Powered air purifying respirators (PAPRs) are used in various applications to provide a user with a constant supply of breathable air in circumstances wherein the air within an ambient in the user's environment is highly contaminated, infectious, polluted, or otherwise unsafe for user consumption. In various industries, an employee working in an environment in which breathing the ambient air of the environment may be hazardous to the user's health may utilize various forms of personal protective equipment (PPE) or breathing apparatuses, such as masks, respirators, ventilators, loose-fitting hoods and/or full-body suits in order to avoid inhaling the potentially hazardous ambient air. Various breathing apparatuses may comprise may be bulky and/or immobile, such that a user's mobility during use may be substantially limited. Further, various PPE may not be configured to provide a level of protection sufficient to ensure that a user is provided with breathable air in highly-contaminated and/or dangerous environments.

In some examples, a PAPR may comprise a self-contained breathing apparatus that utilizes a powered fan system to deliver a consistent flow of breathable air to a user. Often, a PAPR may comprise an in-line filter assembly configured to receive a volume of ambient air passing through the PAPR and purify the air before it is supplied to the user. For example, various PAPRs may comprise a motor-driven blower that may generate a substantially consistent flow of air from the ambient environment along an air flow path so as to deliver a volume of breathable air to a controlled environment within a protective helmet, mask, and or the like, for example, from which a user may breath exclusively breathable air. Blowers may be configured within PAPRs to pull air from the ambient environment and drive the air to the controlled environment at a substantially consistent flow rate. In certain applications, workers utilizing PAPRs may be required to work in confined or narrow spaces. Accordingly, bulky respirator equipment may inhibit the movement of the user while working in the confined or narrow space. Frequently, a significant portion of the overall thickness of a PAPR may be attributed to the thickness of the blower assembly. Further, bulky and complex blower assembly configurations may result in increased manufacturing and production errors, as well as various system inefficiencies and output inaccuracies.

Described herein, and in accordance with example embodiments described herein, is a compact blower assembly designed to minimize the spatial footprint of the blower assembly while maintaining a production output capacity defined by one or more desired blower assembly output parameters. As described herein, exemplary blower assemblies and respirators may be configured to facilitate efficient component interaction and a consolidated physical footprint by removing and/or reconfiguring various blower assembly components and/or geometric features thereof that demand spatial inefficiency and limit the physical compaction of the blower assembly. Such exemplary configuration, as described herein, may correspond to a reduction in costs, as the efficient design of the blower assembly components may result in a reduction of the total number of parts required to produce the blower assembly.

Similarly, the compact blower assembly described in accordance with example embodiments herein may comprise a substantially minimized blower assembly thickness as a result of a spatially efficient configuration of various components of a blower assembly. For example, the compact blower assembly described herein may comprise a blower scroll defined in part by a portion of an external blower assembly casing and/or a respirator housing. In various embodiments, a blower frame element may efficiently function as both a component of the blower scroll and a portion of the respirator housing. As described herein, such a configuration wherein a first blower scroll component is defined by a portion of the respirator and/or blower assembly housing may require a fewer number blower assembly components.

Further, the compact blower assembly described in accordance with example embodiments herein may comprise a minimized blower footprint, which may enable a consolidated blower assembly air flow path between a blower assembly air inlet and a blower air assembly outlet. As described herein, a long and/or geometrically complex air flow path may generate a back pressure within the respirator, which may lead to various errors corresponding to a reduced blower operational efficiency and/or a dampened respirator production output. Accordingly, the blower assembly air flow path may comprise a more direct and/or shorter profile between the blower assembly air inlet 111 and the blower assembly air outlet 113. As described herein, a consolidated blower assembly air flow path may increase the production efficiency of the blower assembly 100 and enable a minimized blower assembly thickness.

In various embodiments, a respirator apparatus may be configured to receive a volume of air from an ambient environment, purify the volume of air by removing at least a portion of the contaminant present within the volume of air (e.g., particulate matter, airborne pathogens, and/or the like), and transmit the purified volume of air to a controlled environment adjacent a mouth of a user wearing the respirator such that the user may inhale a volume of purified air. As described herein, in various embodiments, an exemplary respirator may comprise a respirator housing defining a respirator air inlet that is fluidly engaged with an ambient environment and a respirator air outlet that is fluidly engaged with a controlled environment defined by an airtight an article of personal protective equipment, such as, for example, a facemask, an enclosed hood, and/or the like, that is configured to isolate the controlled environment from the ambient environment. The respirator housing may be configured to receive a volume of air from the ambient environment and may define an air flow path extending between the respirator air inlet and the respirator air outlet such that a volume of air received at the respirator air inlet may travel from the respirator air inlet along the air flow path to the respirator air outlet. In various embodiments, an exemplary respirator may further comprise a filter assembly and a blower assembly, as described herein.

Figure 1B:
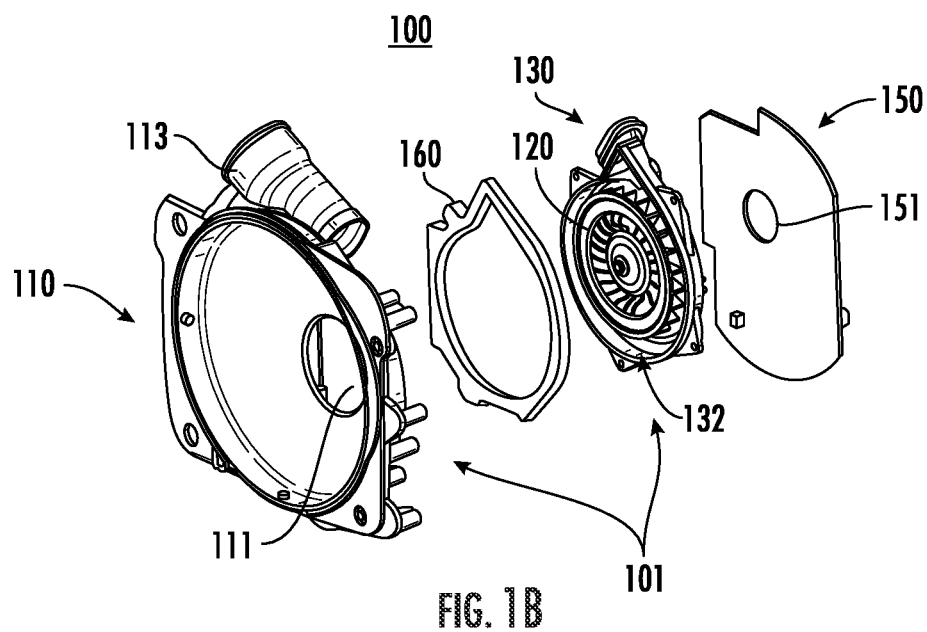

FIGS. 1A-1B illustrate various components of an exemplary respirator apparatus in accordance with various embodiments. In particular, FIGS. 1A-1B illustrate various exploded perspective views of a blower assembly 100 in accordance with various embodiments. In various embodiments, an exemplary blower assembly 100 may be configured to facilitate the flow of air through, for example, a respirator. The blower assembly 100 may be configured to pull a volume of air from the ambient environment into the respirator through a respirator air inlet and facilitate the flow of the received volume of air from the respirator air inlet, along the air flow path, and out of the respirator through a respirator air outlet into a controlled environment. In various embodiments, a blower assembly 100 may comprise an impeller 120, a scroll cover 130, a blower motor 140, and a printed control board assembly (PCBA) 150. The blower assembly 100 may comprise a blower assembly air inlet 111 that is fluidly connected to the respirator air inlet (e.g., either directly or indirectly) such that, in operation, the blower assembly 100 (e.g., an impeller 120) may pull a volume of air from an ambient environment into the respirator air inlet to blower assembly air inlet 111. The blower assembly 100 may further comprise a blower assembly air outlet 113 that may be fluidly connected to a respirator air outlet (e.g., either directly or indirectly) such that, the volume of air received at the blower assembly air inlet 111 may be driven out from the blower assembly air outlet 113 to through the respirator air outlet to a controlled environment, as described herein. In various embodiments, the blower assembly 100 may define a blower assembly air flow path extending between the blower assembly air inlet 111 and the blower assembly air outlet 113 along which the volume of air received by the blower assembly 100 may travel. In various embodiments, the blower assembly air flow path may define a portion of the respirator air flow path. For example, the blower assembly air flow path may define a portion of the respirator air flow path positioned downstream from the blower assembly air inlet 111 and upstream from the blower assembly air outlet 113.

As described herein, the impeller 120 of the blower assembly 100 may define a centrifugal fan component comprising a plurality of radial impeller blades configured to generate airflow within the blower assembly by rotating about a central impeller axis. The blower assembly 100 may be configured such that upon the rotation of the impeller 120, a volume of air may be pulled into the blower assembly air inlet 111, through an impeller intake portion, and pushed in an outward radial direction to a blower assembly air outlet 113. In various embodiments, the rotation of the impeller 120 may cause the volume of air to be pulled into blower assembly air inlet 111 from the ambient environment via the respirator air inlet. In various embodiments, a scroll cover 130 may be configured to at least partially surround the impeller 120 so as direct an air flow generated by the impeller 120 toward a blower assembly air outlet 113. For example, the scroll cover 130 may define a scroll cover cavity 132 configured such that at least a portion of the impeller 120 may be arranged therein. In various embodiments, the scroll cover 130 may be configured to at least partially define the blower assembly air flow path, as described herein.

As described in further detail herein, the scroll cover 130 may be configured to interface with a blower frame element 110. The blower frame element 110 may comprise a structural element including one or more surfaces configured to support and/or house one or more elements of the blower assembly 100. In various embodiments, blower assembly 100 may be configured such that the scroll cover 130 may directly interface the blower frame element 110 so as to define a blower scroll. For example, the blower scroll may define an exterior of an internal scroll flow chamber, which may be defined at least in part by the scroll cover cavity 132. The blower scroll may be configured to house the impeller 120 (e.g., within the internal scroll flow chamber) and define at least substantially all of the blower assembly air flow path extending between the blower assembly air inlet and the blower assembly air outlet. As described herein, the blower assembly 100 may comprise a blower scroll defined collectively by the scroll cover 130 and the blower frame element 110 engaged directly therewith in order to minimize the spatial footprint of the blower assembly 100.

In various embodiments, the blower assembly 100 may further include a gasket 160 configured to define an air-tight seal between the scroll cover 130 and the blower frame element 110 so as to prevent air received through the blower assembly air inlet 111 from being leaked from the internal scroll flow chamber at the interface of the scroll cover 130 and the blower frame element 110. In various embodiments, the blower assembly 100 may further comprise a blower motor 140 configured to drive the rotation of an impeller 120 in order to generate a flow of air through the blower assembly 110. Further, in various embodiments, the blower assembly 100 may comprise a PCBA 150 that may be in electronic communication with one or more components of the blower assembly 100 such as, for example, the blower motor 140. As described herein, the PCBA 150 may comprise one or more geometric features 151 configured such that the PCBA 150 may be interfaced with a back surface of the scroll cover 130 so as to minimize the spatial footprint of the blower assembly 100.

Figure 2A:
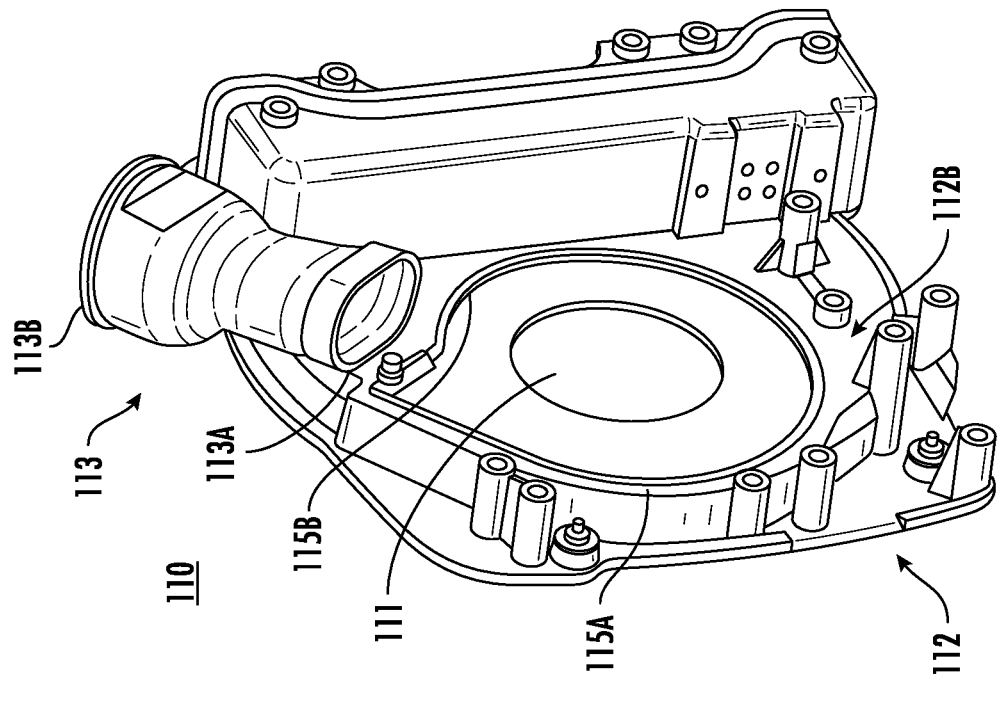
FIGS. 2A-2B illustrate various perspective views of a component of an exemplary blower apparatus in accordance with various embodiments.
Figure 2B:
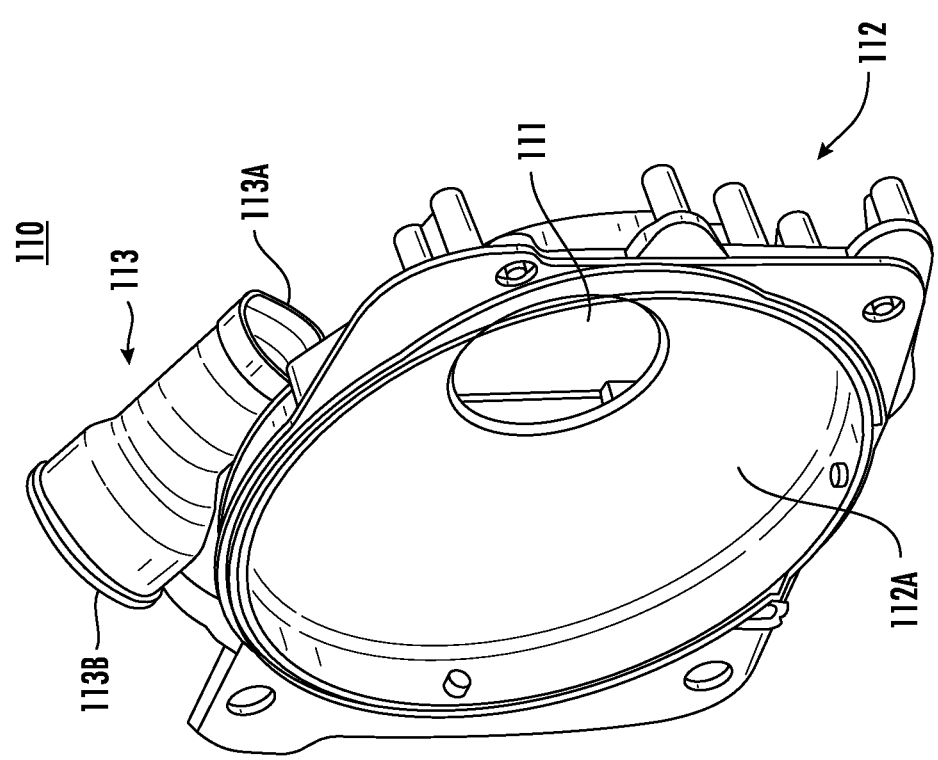

FIGS. 2A-2B illustrate various components of an exemplary respirator apparatus in accordance with various embodiments. In particular, FIGS. 2A-2B illustrate various perspective views of an exemplary blower frame element 110 in accordance with various embodiments. As described herein, a blower frame element 110 may be configured to support and/or house one or more elements of the blower assembly. For example, in various embodiments, the blower frame element 110 may comprise a blower base portion 112. A blower base portion 112 may comprise an at least substantially planar element such as, for example, a wall, a panel, and/or the like configured such that one or more other elements of the blower assembly may be secured thereto, as described herein. As illustrated, the blower base portion 112 may be defined in part by a thickness that extends between an outer base surface 112A and an inner base surface 112B. In various embodiments, at least a portion of the blower frame element 110 may embody at least a portion of the respirator housing, as described herein.

As described herein, the blower frame element 110 may comprise a blower assembly air inlet 111 through which the blower assembly 100 may receive a volume of air traveling along the respirator air flow path. In various embodiments, a blower assembly air inlet 111 may comprise, for example, an orifice, a conduit, and/or the like, configured to receive a volume of air therethrough such that the blower assembly 100 may be fluidly connected to the respirator air flow path. Accordingly, the blower assembly air inlet 111 may define a first end of the blower assembly air flow path of the blower assembly 100, as described herein. For example, the blower assembly air inlet 111 may comprise an orifice extending through the blower base portion 112 from the outer blower base surface 112A to the inner blower base surface 112B. In various embodiments, the blower assembly air inlet 111 may comprise a blower assembly air inlet cross-sectional area of at least approximately between 700 mm$^2$ and 3000 mm$^2$ (e.g., between 1500 mm$^2$ and 2200 mm$^2$).

In various embodiments, the blower frame element 110 (e.g., the blower base portion 112) may be configured to engage one or more portions of a respirator housing, as described herein, so as to at least partially stabilize the arrangement of the blower assembly within the respirator housing. As described herein, in various embodiments wherein the blower assembly defines a portion of a respirator air flow path, the blower frame element 110 may be configured such that the outer blower base surface 112A may be positioned upstream from the inner blower base surface 112B. In various embodiments, for example, the outer blower base surface 112A may be configured so as to direct a volume of air travelling along a respirator air flow path to the blower assembly air inlet 111. As a non-limiting example, the outer blower base surface 112A may have a cone-shaped configuration so as to funnel a volume of air into the blower assembly air inlet 111.

In various embodiments, the inner blower base surface 112B may be configured to physically engage at least a portion of the scroll cover (e.g., a lower perimeter surface). As described in further detail herein, the inner blower base surface 112B may be configured such that the scroll cover may be secured thereto in order to define an internal scroll flow chamber. In such an exemplary circumstance, the blower frame element 110 (e.g., at least a portion of the inner blower base surface 112B) and the scroll cover secured thereto may collectively define the blower scroll, configured to house the impeller and contain and/or direct the flow of air within the blower scroll, as described in further detail herein. In various embodiments, the inner blower base surface 112B may comprise one or more blower base geometric features 115A-115B configured to facilitate a preferred blower scroll configuration. For example, in various embodiments, one or more blower base geometric features 115A-115B may be configured to facilitate a secure and/or air-tight interface between the inner blower base surface 112B of the blower base portion 112 and the scroll cover. Further, in various embodiments, one or more blower base geometric features 115A-115B may be configured to facilitate a more efficient manufacturing, production, and/or assembly processes associated with the blower assembly. Further still, in various embodiments, one or more blower base geometric features 115A-115B may be configured to optimize one or more flow conditions within the internal scroll flow chamber (e.g., along the blower assembly air flow path) in order to increase the efficiency and/or efficacy of the blower assembly. Similarly, one or more blower base geometric features 115A-115B may be configured so as to reduce the spatial footprint of the blower assembly. In various embodiments, one or more blower base geometric features 115A-115B of the inner blower base surface 112B may comprise one or more material protrusions, recesses and/or profiles. For example, one or more blower base geometric features 115A-115B may be defined at least in part by a shape corresponding to the shape of at least a portion of the scroll cover.

By way of non-limiting example, as illustrated in FIG. 2B, a first blower base geometric feature 115A comprises an at least substantially flat portion of the inner blower base surface 112B having a curved profile configured to correspond to the curvature of a portion of a lower perimeter surface of an exemplary scroll cover that may be engaged therewith. In such an exemplary circumstance, blower base geometric feature 115A may be configured so as to facilitate an at least substantially air-tight interface with the exemplary scroll cover along the portion of the lower perimeter surface engaged therewith. As a further illustrated non-limiting example, a second blower base geometric feature 115B may comprise a material protrusion extending from the inner blower base surface 112B directionally away from the thickness of the blower base portion 112. In such an exemplary circumstance, blower base geometric feature 115B may be configured to extend along the inner blower base surface 112B in a pattern that corresponds to the curvature of at least a portion of a lower perimeter surface of an exemplary scroll cover that may be engaged therewith. The blower base geometric feature 115B may be configured to physically engage an external surface and/or an internal surface of the corresponding portion of the exemplary scroll cover so as to constrain the relative motion of the scroll cover in one or more directions.

In various embodiments, the blower frame element 110 may further comprise a blower assembly air outlet 113. In various embodiments, a blower assembly air outlet 113 may comprise, for example, an orifice, a conduit, and/or the like, through which a volume of air traveling along the blower assembly air flow path may be pushed so as to be dispensed from the blower assembly 100. Accordingly, the blower assembly air outlet 113 may define a second end of the blower assembly air flow path of the blower assembly 100 (e.g., opposite a first end defined by a blower assembly air inlet 111). In various embodiments, the blower assembly air outlet 113 may be fluidly connected to the respirator air flow path such that a volume of air dispense from the blower assembly air outlet 113 may continue to travel along the respirator air flow path to a respirator air outlet, where the volume of air may be dispensed from the respirator into a controlled environment, as described herein. Alternatively, the blower assembly air outlet 113 may define the respirator air outlet such that a volume of air pushed through the blower assembly air outlet 113 by the blower assembly may be dispensed directly into the controlled environment.

As illustrated in FIGS. 2A-2B, an exemplary blower assembly air outlet 113 may comprise a conduit having a length extending between a first blower assembly air outlet end 113A and a second blower assembly air outlet end 113B. For example, the illustrated blower assembly air outlet 113 may be configured to receive a volume of air from the blower scroll at the first blower assembly air outlet end 113A (e.g., via a blower scroll outlet) and direct the volume of air along the length of the blower assembly air outlet 113 through the second blower assembly air outlet end 113B into a controlled environment. As described herein, an exemplary blower assembly air outlet 113 embodied as a conduit may be configured such that the length of the blower assembly air outlet 113 may be minimized in order to minimize the length of the respirator air flow path arranged downstream from the impeller and, thus, minimize the amount of back pressure generated by the configuration of the blower assembly. In various embodiments, the blower assembly air outlet 113 may comprise a cross-sectional configuration configured to minimize the thickness of the blower assembly air outlet 113 while facilitating a flowrate corresponding to an optimized respirator output flowrate, as described herein, such as, for example, a substantially rounded cross-sectional configuration (e.g., an at least substantially oval-shaped cross-sectional configuration). For example, the blower assembly air outlet 113 may comprise a blower assembly air outlet cross-sectional area of at least approximately between 175 $mm^2$ and 2000 $mm^2$ (e.g., between 750 $mm^2$ and 1250 $mm^2$). In various embodiments, an exemplary blower frame element may comprise either a singular component or a plurality of distinct modular components.

Figure 3A:
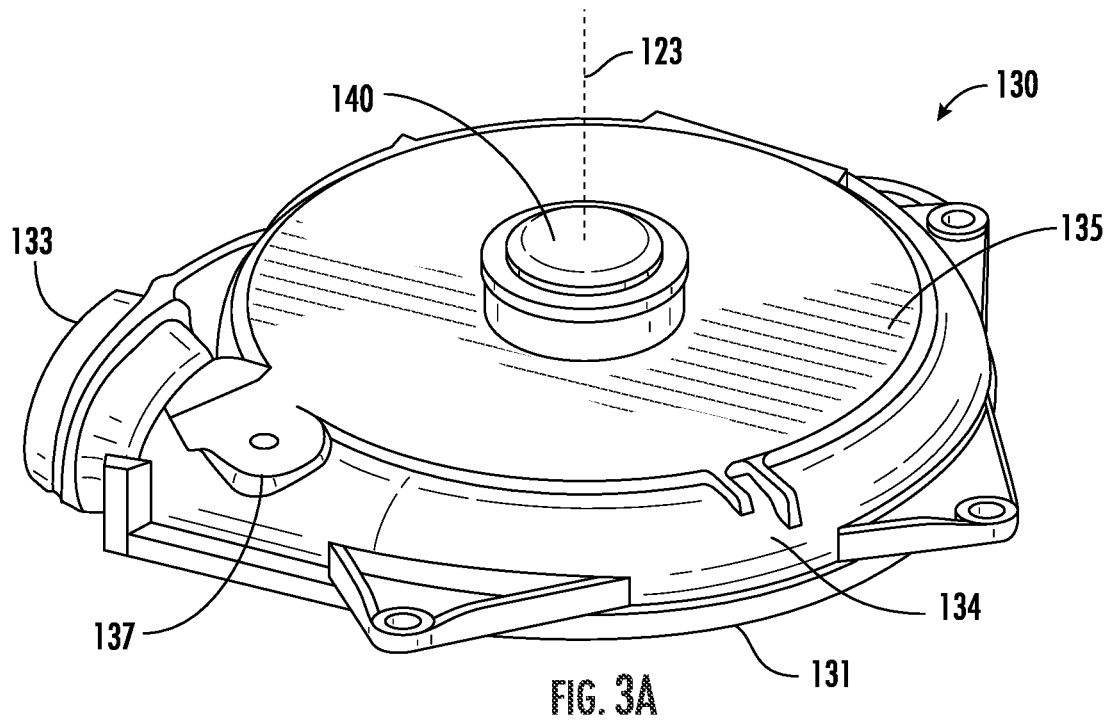
FIGS. 3A-3B illustrate various perspective views of a component of an exemplary blower apparatus in accordance with various embodiments.
Figure 3B:
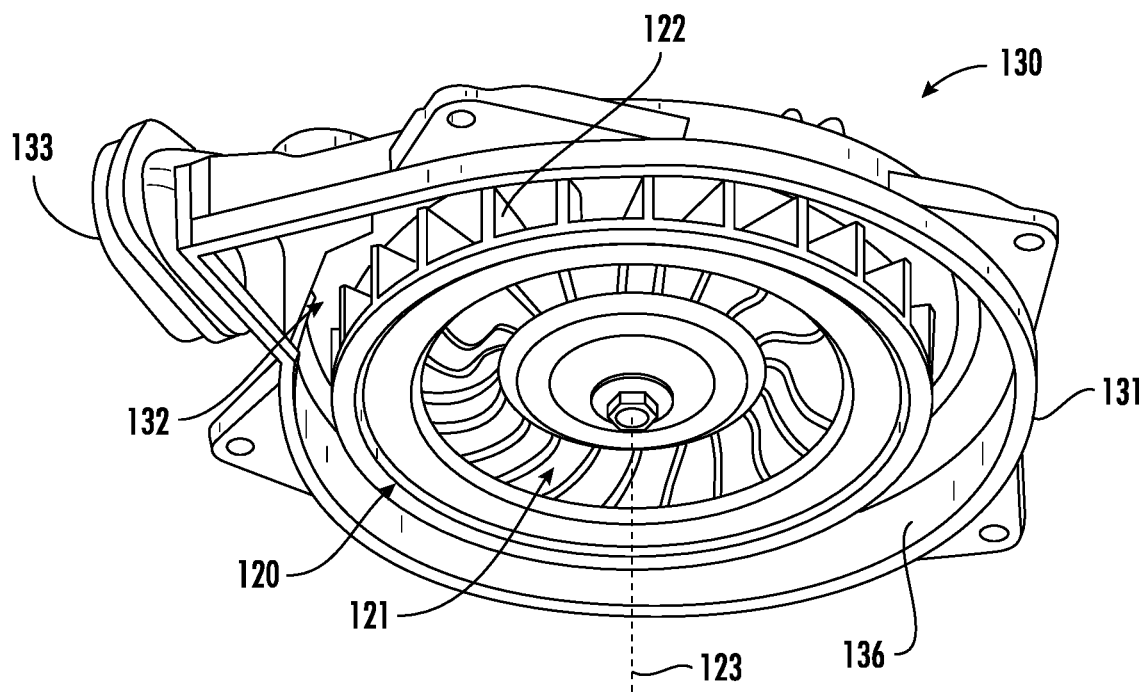

FIGS. 3A-3B illustrate various components of an exemplary respirator apparatus in accordance with various embodiments. In particular, FIGS. 3A-3B illustrate various perspective views of an exemplary scroll cover 130 and an exemplary impeller 120 in accordance with various embodiments. A scroll cover 130 may be configured to contain and/or direct a volume of air received by the blower assembly toward a blower assembly air outlet, as described herein. In various embodiments, the scroll cover 130 may comprise a substantially round (e.g., circular) and concave configuration defined in part by one or more rounded scroll cover sidewalls 134 extending between a lower perimeter surface 131 and a back surface 135. As described herein, in various embodiments, the one or more rounded scroll cover sidewalls 134 and the scroll cover back surface 135 may comprise either a singular component or a plurality of distinct components that may be assembled to collectively define at least a portion of the scroll cover 130. In various embodiments, the one or more rounded scroll cover sidewalls 134 may extend around a central impeller axis 123 so as to collectively define at least a portion of an outer perimeter of the scroll cover 130. Further, in various embodiments, the one or more rounded scroll cover sidewalls 134 may extend at least substantially linearly between the lower perimeter surface 131 and the back surface 135, for example, in a direction at least substantially parallel to the central impeller axis 123. Alternatively, at least a portion of the one or more rounded scroll cover sidewalls 134 may comprise a non-linear profile such that the one or more rounded scroll cover sidewalls 134 are defined at least in part by a radius of curvature measured between the lower perimeter surface 131 and the back surface 135.

In various embodiments, the lower perimeter surface 131 of the scroll cover 130 may be defined at least in part by the thickness of the one or more scroll cover sidewalls 134 at a lower boundary area of the scroll cover 130. For example, a thickness of the one or more scroll cover sidewalls 134 may extend perpendicularly between an external scroll cover surface and an internal scroll cover surface 136 in a radially outward direction away from the central impeller axis 123. In various embodiments, the lower boundary area of the scroll cover 130 may comprise an at least substantially planar boundary of the scroll cover 130 positioned at least substantially opposite the back surface 135 of the scroll cover 130 as measured along the central impeller axis 123. For example, as illustrated in FIG. 3B, the lower boundary area of the scroll cover 130 may be defined collectively by the lower perimeter surface 131 and the cross-sectional area within the lower perimeter surface 131. In various embodiments, for example, at least a portion of the lower boundary area of the scroll cover 130 may be at least substantially parallel to the back surface 135.

In various embodiments, the scroll cover 130 may comprise a scroll cover cavity 132 defined by the concave configuration of the scroll cover 130. The scroll cover cavity 132 may comprise an internal portion of the scroll cover 130 extending between a lower boundary area of the scroll cover 130 and an internal scroll cover surface 136, as described herein. In various embodiments, the scroll cover cavity 132 may be defined at least in part by the internal scroll cover surface 136. As non-limiting examples, the scroll cover cavity 132, based at least in part on the configuration of the internal scroll cover surface 136, may be at least substantially dome-shaped, at least substantially cylindrical, and/or the like.

As described herein, the scroll cover 130 of an exemplary blower assembly may be configured to directly engage a portion of the blower frame element of the blower assembly such that the scroll cover 130 and the portion of the blower frame element engaged therewith collectively define a blower scroll. In various embodiments, a portion of the scroll cover 130, such as, for example, the lower perimeter surface 131, may be configured to define at least a portion of an interface between the scroll cover 130 and the blower frame element. For example, the lower perimeter surface 131 of the scroll cover 130 may be configured to engage a corresponding (e.g., similarly configured and substantially flat) portion of the inner blower base surface such that the interface between the scroll cover 130 and the blower frame element may be at least substantially flush and continuous about the lower perimeter surface 131. In such an exemplary circumstance, the lower perimeter surface 131 may be engaged with the inner blower base surface of the blower frame element such that at least a portion of the inner blower base surface is positioned adjacent the lower boundary area of the scroll cover 130. In various embodiments, the portion of the inner blower base surface within the perimeter defined by the interface between the blower frame element and the scroll cover 130 may (e.g., the portion of the inner blower base surface arranged adjacent the lower boundary area of the scroll cover 130) may define a portion of an internal blower scroll surface. For example, an internal blower scroll surface may be defined at least in part by the one or more internal scroll cover surface(s) 136 and said portion of the inner blower base surface positioned within the perimeter defined by the interface between the blower frame element and the scroll cover 130. In various embodiments, the scroll cover 130 may be secured to the blower frame element by various permanent, semi-permanent, and/or non-permanent fastening means such as, for example, screws, latches, fasteners, clips, hooks, adhesives, interlocking geometric features, and/or the like.

In various embodiments, the blower scroll may comprise an internal scroll flow chamber defined at least in part by a space extending between an internal scroll cover surface 136 and the portion of the inner blower base surface positioned within the perimeter of the interface between the blower frame element and the scroll cover 130. For example, the internal scroll flow chamber may comprise the scroll cover cavity 132. In various embodiments, the blower scroll may be further configured to house an impeller 120 within the internal scroll flow chamber (e.g., between the internal scroll cover surface 136 and the inner blower base surface of the blower frame element). As described herein, the blower scroll may be configured such that the flow of air generated by the impeller 120 housed therein may be dispensed from the blower air output of the blower assembly in a substantially consistent manner according to at least one desirable output airflow conditions (e.g., output flowrate, output pressure, output air volume, and/or the like). For example, in various embodiments, one or both of the blower frame element and the scroll cover 130 interfaced thereto may include one or more features, such as, for example, dimensional features, geometric features, and/or the like, in order to optimize one or more flow conditions within the internal scroll flow chamber in order to increase the efficiency and/or efficacy of the airflow through the blower scroll.

In various embodiments, the blower scroll may be configured such that the airflow generated by the impeller 120 may cause a volume of air to be pulled into a blower scroll air inlet. The blower scroll air inlet may be defined as an orifice, channel, and/or the like through which the blower scroll may receive a volume of air travelling along a respirator air flow path. In various embodiments, wherein the blower scroll is defined by a portion of the blower frame element and an exemplary scroll cover 130 secured thereto, the blower assembly air inlet, as described herein, may function as the blower scroll air inlet. In various embodiments, for example, the cross-sectional area of the blower assembly air inlet may be at least substantially smaller than that of the lower boundary area of the scroll cover 130, and further, the blower assembly air inlet may extend through a portion of the blower frame element (e.g., a portion of the inner blower base surface) that is within the perimeter defined by the interface between the blower frame element and the scroll cover 130. In such an exemplary circumstance, the blower assembly air inlet of the blower assembly may define the blower scroll air inlet.

In various embodiments, the blower scroll may be configured to contain and/or direct the flow of air along a portion of the blower assembly air flow path extending through the internal scroll flow chamber. For example, the interface between the scroll cover 130 and the blower frame element may comprise an at least substantially air-tight seal so as to prevent a volume of air received by the blower scroll from being leaked from within the internal scroll flow chamber upstream from the blower scroll air outlet. As described herein, the blower scroll air inlet may be fluidly connected to a blower scroll air outlet of the blower scroll via the internal scroll flow chamber. In various embodiments, the blower scroll air outlet may comprise, for example, an orifice, a conduit, and/or the like, through which a volume of air within the internal flow chamber may be pushed so as to be dispensed from the blower scroll. In various embodiments, the blower scroll air outlet may be defined at least in part by a scroll cover air outlet 133. For example, as illustrated in FIGS. 3A-3B, the scroll cover 130 may be configured such that the scroll cover air outlet 133 may alone define the blower scroll air outlet. Alternatively, in various embodiments, the blower scroll air outlet may be defined in part by the scroll cover air outlet 133 and in remaining part by an adjacent portion of the blower frame element. In various embodiments wherein the blower assembly air outlet is embodied as a conduit, as described herein, the blower scroll air outlet (e.g., the scroll cover air outlet 133) may be configured to engage a first blower assembly air outlet end so as to fluidly connect the internal scroll flow chamber to the blower assembly air outlet. Alternatively, in various embodiments wherein the blower assembly air outlet of the blower assembly is embodied as an orifice, the blower assembly air outlet and/or the respirator air outlet may define the blower scroll air outlet, as described herein.

As illustrated in FIGS. 3A-3B and as described above, the scroll cover 130 comprises a scroll cover cavity 132 that may be configured to house at least a portion of an impeller 120 in various embodiments. For example, in an exemplary embodiment wherein the scroll casing 130 is interfaced with a blower frame element along the lower perimeter surface 131 such that said two components of the blower assembly collectively define a blower scroll, the blower scroll may be configured to house an impeller 120 within an internal scroll flow chamber (e.g., between the internal scroll cover surface 136 and the inner blower base surface of the blower frame element). In various embodiments, the impeller 120 may define a centrifugal fan (e.g., a radial fan) element configured to generate a flow of air along, for example, a respirator air flow path (e.g., a blower assembly air flow path) by utilizing a rotational motion of a plurality of radial impeller blades 122 about a central impeller axis 123 so as to displace one or more volumes of air present within a respirator air flow path. In various embodiments, an impeller 120 may comprise a plurality of radial impeller blades 122 configured to generate airflow within the blower assembly by rotating about a central impeller axis 123. For example, a blower assembly may be configured such that the rotation of the impeller 120 (e.g., the plurality of radial impeller blades 122) may pull a volume of air from an ambient environment and/or an upstream portion of the respirator air flow path into the blower assembly via the blower assembly air inlet. As described herein, wherein the blower assembly air inlet is defined within the blower frame element and wherein the blower frame element defines at least a portion of a blower scroll, the blower assembly air inlet may function as the blower scroll air inlet, through which the impeller 120 may pull a volume of air into the blower scroll.

An impeller 120 may comprise an impeller intake portion 121 through which an impeller 120 may pull and/or receive a volume of air. In various embodiments, the impeller 120 may be arranged such that the impeller intake portion 121 is at least substantially aligned with the blower assembly air inlet (e.g., the blower scroll air inlet) and positioned at least substantially adjacent thereto. For example, the impeller air intake portion 121 may be positioned such that the impeller central axis 123 extending therethrough extends through the center of the blower scroll air inlet in a direction at least substantially perpendicular to the cross-sectional area of the blower assembly air inlet. In various embodiments, the impeller 120 may further comprise an impeller frame element configured to allow the impeller 120 to be structurally attached to one or more surfaces of the blower assembly while still allowing for the rotational movement of the impeller 120 (e.g., plurality of radial impeller blades 122) about the central impeller axis 123. For example, the impeller frame element may be configured to secure the impeller 120 to the blower frame element (e.g., an inner blower base surface) so as to constrain the relative motion between the impeller and the blower frame element and preserved alignment of the central impeller axis 123 with the blower assembly air inlet. Alternatively, or additionally, the impeller frame element may be configured to secure the impeller 120 to one or more surfaces of the scroll cover 130.

In various embodiments, the impeller 120 may be configured to pull a volume of air into the blower scroll air inlet (e.g., the blower assembly air inlet) and through an impeller intake portion 121 as the impeller 120 rotates about the central impeller axis 123. In various embodiments, the rotation of the impeller 120 may further cause the volume of air pulled through the impeller intake portion 121 to be subsequently pushed by the plurality of radial impeller blades 122 in an outward radial direction (e.g., away from the central impeller axis 123) within the internal scroll flow chamber. As described herein, the scroll cover 130 (e.g., the blower scroll) may be configured to direct the volume of air pushed by the plurality of radial impeller blades 122 towards a scroll cover air outlet (e.g., a blower scroll outlet). In various embodiments, the rotation of the impeller 120 may cause a volume of air to be pulled from an ambient environment into a respirator air inlet and along a respirator air flow path to the blower assembly air inlet. Further, in various embodiments wherein the respirator air outlet is distinguished from the blower assembly air outlet and positioned downstream therefrom, the rotation of the impeller 120 may cause a volume of air pushed from the blower assembly air outlet to be further pushed along a respirator air flow path to a respirator air outlet and through to a controlled environment.

In various embodiments, an impeller 120 may be connected to a blower motor 140 configured to drive the rotation of the impeller 120 about the central impeller axis 123, as described herein. In various embodiments, a blower motor 140 may comprise, for example, a rotary assembly and a stator configured to translate one or more electrical signals into the physical motion of the impeller 120. For example, in various embodiments, the blower motor 140 may be configured to receive one or more electrical signals from a PCBA, as described herein. In response, the blower motor 140 may cause at least a portion of the rotary assembly attached thereto (e.g., a rotary shaft) to rotate. In various embodiments, a portion of the impeller 120 may be secured to the rotary assembly such that the rotation of a portion of the rotary assembly may drive the rotational motion of the impeller 120. Accordingly, the impeller 120 may be controlled according to one or more operating parameters of the blower motor 140. As a non-limiting example, in various embodiments, the blower motor 140 may be configured to drive a maximum production output of approximately 68 mm $H_2O$. Further, in various embodiments, the blower assembly motor may be configured to produce an output airflow from an exemplary respirator air outlet of at least 107 liters per minute (LPM). In various embodiments, blower motor 140 may comprise any type of motor appropriate for use with a blower assembly 100 as described herein (e.g., operable with a scroll fan). For example, the blower motor 140 may comprise a direct current (DC) motor, such as, for example, a brushed DC motor, a brushless DC motor, and/or the like. Alternatively, in various embodiments, the blower motor 140 may comprise an alternating current (AC) motor.

As described herein, the back surface 135 of the scroll cover 130 may comprise an at least substantially flat surface extending along a portion of the exterior of the scroll cover 130. In various embodiments, the back surface 135 may be configured to receive at least a portion of an exemplary PCBA, as described herein. For example, the back surface 35 may be at least substantially flat so as to facilitate a spatially efficient interface between the PCBA and the back surface, wherein a substantially flat PCBA may be uniformly secured to the entirety of back surface 35 in an at least substantially flush manner. As described herein, the direct engagement of a PCBA across substantially an entire back surface 35 may facilitate a minimized blower assembly thickness by avoiding a configuration wherein the back surface 35 of the scroll cover 130 and a corresponding portion of a PCBA secured thereto comprise a disjointed interface.

Figure 4:
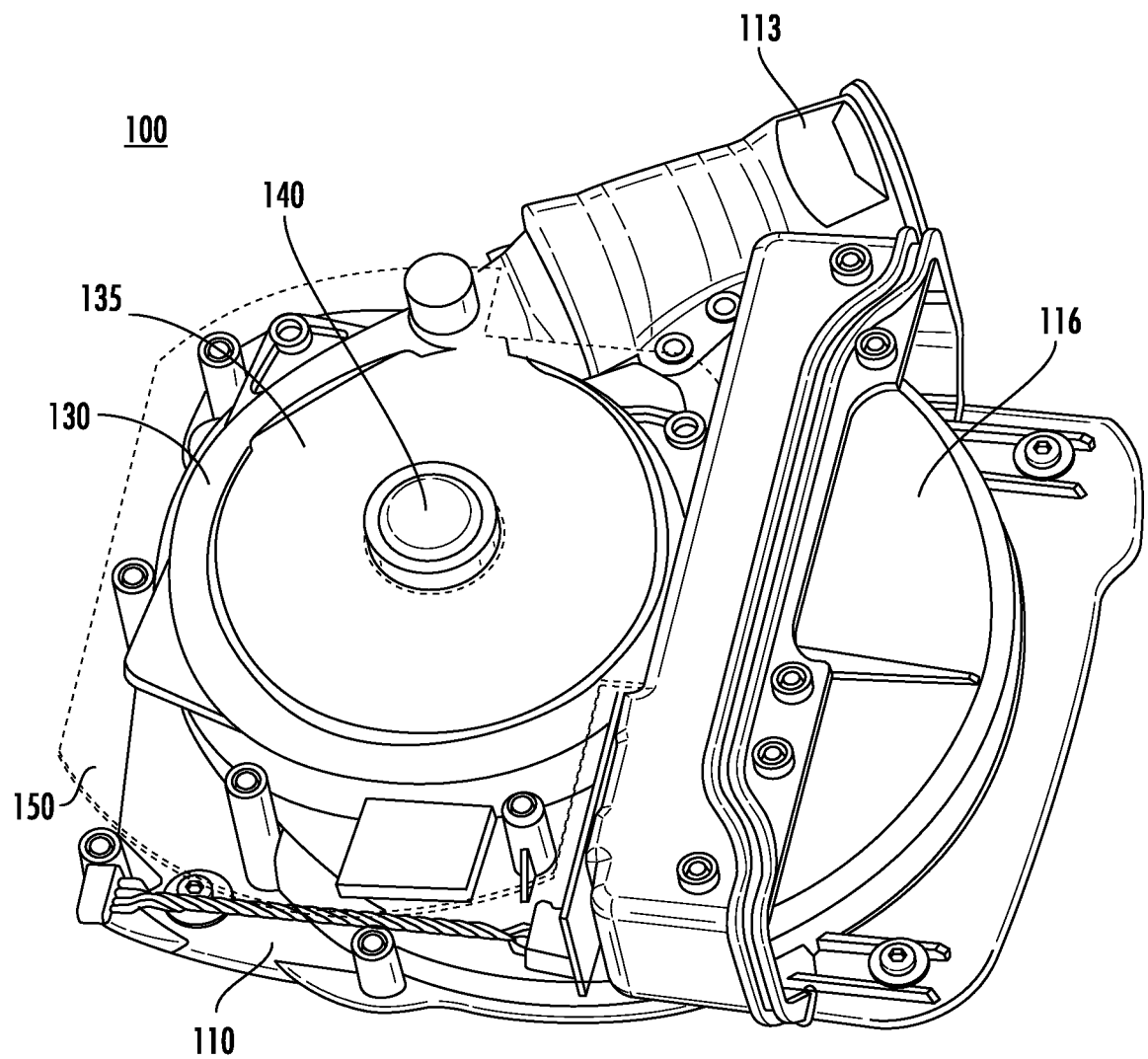
FIG. 4 illustrates a perspective view of a component of an exemplary blower apparatus in accordance with various embodiments.

FIG. 4 illustrates a perspective view of a component of an exemplary respirator apparatus in accordance with various embodiments. In particular, FIG. 4 illustrates an exemplary blower assembly 100 in accordance with various embodiments. The exemplary blower assembly 100 illustrated in FIG. 4, may comprise a compact blower assembly configuration designed to minimize the spatial footprint of the blower assembly 100 while maintaining a production output capacity defined by one or more desired blower assembly output parameters (e.g., output flowrate, output pressure, output air volume, and/or the like). For example, the blower assembly 100 may be configured to facilitate efficient component interaction and a consolidated physical footprint by removing various blower assembly components and/or geometric features thereof that demand spatial inefficiency and limit the physical compaction of the blower assembly 100.

For example, an exemplary blower assembly 100 may be defined at least in part by a blower assembly length, blower assembly width, and blower assembly height (e.g., thickness). As illustrated in FIG. 4, the blower assembly length, blower assembly width, and blower assembly thickness of an exemplary blower assembly 100 may correspond to the dimensional configurations of the blower assembly 100 in the x-direction, y-direction, and z-direction, respectively. In various embodiments, an exemplary compact blower assembly may comprise a blower assembly length of at least substantially between 50 mm and 300 mm (e.g., between 150 mm and 200 mm). In various embodiments, an exemplary compact blower assembly may comprise a blower assembly width of at least substantially between 50 mm and 300 mm (e.g., between 150 mm and 200 mm). As an illustrative example, in various embodiments blower assembly height (e.g., thickness) may be measured in a direction that extends parallel to the central impeller axis, as described herein. Measured in such a direction, the thickness of an exemplary blower assembly 100 described herein may be at least substantially minimized due at least in part to the spatially efficient configuration of the exemplary blower assembly 100 described herein. In various embodiments, the thickness of an exemplary blower assembly 100 may be at least substantially minimized so as to comprise a thickness of at least substantially between 10 mm and 60 mm (e.g. between 30 mm and 40 mm). For example, such an exemplary blower assembly thickness may correspond to a reduction in blower assembly thickness of at least substantially between 3 mm and 20 mm (e.g. between 8 mm and 15 mm). For example, in various embodiments wherein the blower frame element 110 defines at least a portion of an external blower assembly casing and/or a respirator housing 11 and is further configured to define a portion of the blower scroll, as described herein, one or more structural and/or directional air flow components positioned upstream from the internal scroll flow chamber of the blower scroll may be rendered obsolete. In particular, by configuring the blower assembly 100 such that a portion of the blower scroll is defined by an external blower assembly frame element and/or respirator housing portion (e.g., the blower frame element 110), and further such that the blower assembly air inlet defines the blower scroll air inlet, an exemplary second blower scroll casing component may be removed from the blower assembly (e.g., in various embodiments wherein the blower scroll comprise two scroll casing components interfaced together to define a blower scroll).

Further, in various embodiments, the blower assembly 100 is configured such that the blower assembly air inlet 111 is arranged at the blower frame element 110. As described herein, where the blower frame element 110 may comprise a portion of the blower scroll, the internal scroll flow chamber is positioned directly adjacent the blower assembly air inlet 111 such that the blower assembly air inlet 111 may define the blower scroll air inlet. In such an exemplary circumstance, the length of the blower assembly air flow path extending between the blower assembly air inlet 111 and the blower scroll air inlet is at least substantially minimized (e.g., reduced to zero). Accordingly, the blower assembly air flow path may comprise a more direct and/or shorter profile between the blower assembly air inlet 111 and the blower assembly air outlet 113. As described herein, a consolidated blower assembly air flow path may increase the production efficiency of the blower assembly 100 and enable a minimized blower assembly thickness.

Figure 5:
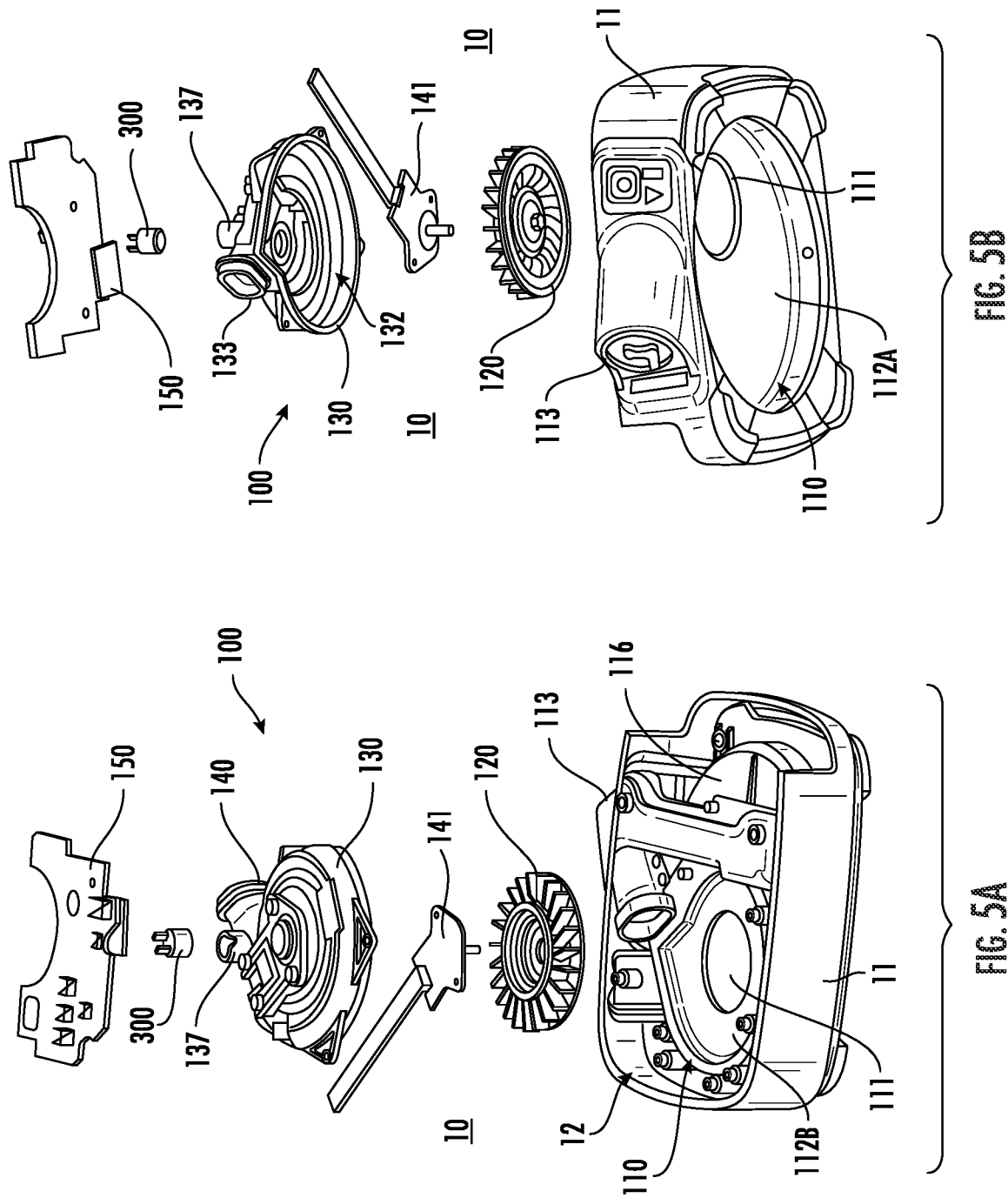
FIGS. 5A-5B illustrate exploded perspective views of various components of an exemplary respirator apparatus in accordance with various embodiments.

FIGS. 5A-5B illustrate exploded perspective views of various components of an exemplary respirator apparatus in accordance with various embodiments. In particular, FIG. 5A and FIG. 5B illustrate an exploded top perspective view and an exploded bottom perspective view, respectively of an exemplary blower assembly 100 arranged relative to a respirator housing 11 in accordance with various embodiments. As described herein, the blower assembly 100 may comprise a blower frame element 110 configured to embody at least a portion of an exterior of the blower assembly 100 and/or at least a portion of the respirator. For example, an exterior portion of the blower assembly 100 may be defined by an outer casing and/or outer boundary of the blower assembly 100. The blower frame element 110 may define a blower assembly air inlet 111 extending through the thickness thereof. Further, the blower frame element 110 may engage a portion of a scroll cover 130 (e.g., an interface surface) configured to be secured to the inner blower base surface 112B such that the cover scroll 130 and the portion of the blower frame element 110 interfaced therewith may collectively define a blower scroll configured to house an impeller 120 therein. For example, a portion of the blower frame element 110 interfaced with the scroll cover 130 may comprise a substantially flat planar surface. In various embodiments, the blower scroll may comprise an internal scroll flow chamber comprising a cavity defined between the internal cover scroll surface and the portion of the blower frame element 110 interfaced therewith.

Further, in various embodiments, the blower assembly 100 may comprise a blower motor 140 configured to drive the rotation of the impeller 120 within an internal scroll flow chamber. In various embodiments, at least a portion of the blower motor 140 may be housed within the scroll cover 130 so as to minimize the distance between the blower motor 140 and the impeller 120, and thus, minimize the amount of space occupied by the blower motor 140 and/or related motor components, such as, for example, a stator, a rotary assembly, a bearing assembly, various sensors, and/or an electrical connection elements 141 configured to facilitate electronic communication between the blower motor 140 and a PCBA 150.

An exemplary blower assembly 100 may further comprise a singular PCBA 150 secured to a substantially flat back surface 135 of the scroll cover 130. As described herein, the PCBA 150 may comprise one or more physical features configured to accommodate the spatial requirements of one or more blower assembly components. For example, the PCBA 150 may define an orifice extending therethrough that may be configured to receive at least a portion of the blower motor 140 and/or the scroll cover 130. PCBA 150 may comprise a singular printed circuit board including both motor control circuitry configured to electronically communicate with the blower motor 140 so as to facilitate control thereof, and respirator operation circuitry configured to electronically communicate with various electrical components of an exemplary respirator described herein so as to facilitate operability thereof. The singular PCBA 150 embodies a consolidated design configured to reduce the number of components within the blower assembly 100 so as to minimize the amount of space occupied by the blower assembly 100, as well as the manufacturing and production costs associated therewith. In various embodiments, the blower assembly 100 may further comprise a beeper assembly 300. For example, the beeper assembly 300 may comprise a beeper element configured to be in electronic communication with the PCBA 150 so as to facilitate the transmission of one or more electrical signals therebetween in order to enable an alert functionality of the beeper assembly 300. For example, the beeper element may be configured to communicate with one or more components of the blower assembly 100 such that the beeper assembly may generate an alert signal upon determining that that one or more operating conditions of the blower assembly 100 (e.g., output flowrate, battery status, and/or the like) at a given instance is outside of a predetermined acceptable range. In various embodiments, the beeper assembly 300 may be arranged in any position about the blower scroll (e.g., at the scroll cover 130) wherein the beeper assembly remains operably capable of executing the beeper functionality described above. For example, the scroll cover 130 may comprise a beeper element interface 137 configured to secure the beeper assembly 300 at a location adjacent the blower scroll air outlet in order to facilitate the integration of the beeper subassembly 300 into the exemplary blower assembly 100.

As illustrated in FIGS. 5A-5B, the exemplary blower assembly 100 may be configured to fit within a respirator housing 11. In various embodiments, the respirator housing may comprise an outer casing defining an exterior portion of the respirator apparatus. In various embodiments, the respirator housing 11 may be configured such that at least substantially all of a blower assembly 100 may be disposed within an internal respirator housing portion 12 defined at least in part by one or more sidewalls of the respirator housing 11. As described herein, the one or more sidewalls of the respirator housing 11 may define at least a portion of the thickness of the respirator 10. For example, the internal respirator housing portion 12 may be further defined by the blower frame element 110. For example, the blower frame element 110 may be configured to engage at least a portion of the one or more sidewalls of the respirator housing 11. For example, in various embodiments, the blower frame element 110 may comprise a second blower frame element portion 116 configured based at least in part on the shape and/or configuration of one or more respirator components positioned adjacent thereto so as to maximize the spatial efficiency of the blower assembly and further facilitate the compact configuration described herein. In various embodiments wherein the blower frame element 110 defines a portion of the respirator housing 11, the outer blower base surface 112A may define an external surface of the respirator housing 11. Further, as described herein, the respirator housing 11 may comprise an external housing compartment defined in part by the outer blower base surface 112A.

As described herein, a compact configuration of an exemplary blower assembly 100 may be defined by a minimized blower assembly thickness. In various embodiments, such an exemplary compact blower assembly configuration may enable a compact respirator configuration, wherein the respirator apparatus thickness may be minimized to a similar extent. For example, in various embodiments, a compact respirator configuration may be defined at least in part by a minimized respirator thickness, wherein the reduction in respirator thickness realized by the respirator may be at least substantially proportional and/or equal to a reduction in blower assembly thickness associated with the minimized respirator thickness.

Figure 6:
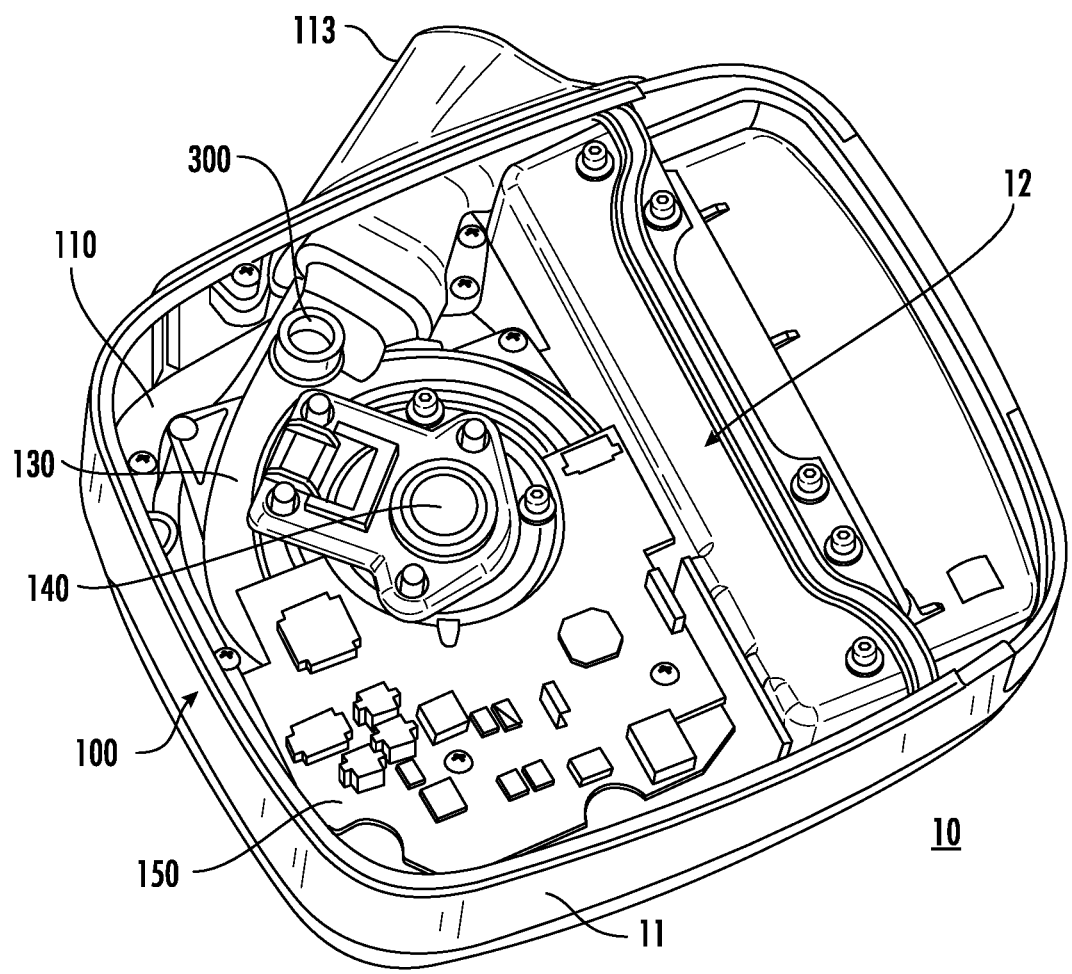
FIG. 6 illustrates a perspective view of an exemplary respirator apparatus in accordance with various embodiments.

FIG. 6 illustrates a perspective view of an exemplary respirator apparatus in accordance with various embodiments. In particular, FIG. 6 illustrates a top perspective view of an exemplary blower assembly 100 arranged within a respirator housing 11 in accordance with various embodiments. As illustrated in FIG. 6, the respirator assembly 10 may be configured such that an exemplary blower assembly 100 may be arranged within an internal respirator housing portion 12 defined by the one or more sidewalls of the respirator housing 11. In various embodiments, as described herein, the respirator 10 may define a respirator air flow path extending between a respirator air inlet and a respirator air outlet, along which the volume of air received by the respirator 10 may travel. In various embodiments, the respirator air flow path may comprise the blower assembly air flow path, as described herein, defined as a portion of the respirator air flow path positioned downstream from the blower assembly air inlet and upstream from the blower assembly air outlet along which a volume of air received by the blower assembly 100 may travel. In various embodiments, a respirator air outlet may comprise, for example, an orifice, a conduit, and/or the like, through which a volume of air traveling along the respirator air flow path may be pushed so as to be dispensed from the respirator 10. Accordingly, the respirator air outlet may define a second end of the respirator air flow path (e.g., opposite a first end defined by a respirator air inlet).

As described herein, a respirator air outlet may be fluidly connected to a controlled environment such that a volume of air pushed through a respirator air outlet (e.g., by a blower assembly 100) may be dispensed from the respirator into the controlled environment. In various embodiments, as illustrated in FIG. 6, the respirator 10 may be configured such that the blower assembly air outlet 113 of the blower assembly 100 may define the respirator air outlet. In such an exemplary circumstance, a volume of air pushed through the blower assembly air outlet 113 by the blower assembly 100 may be dispensed into the controlled environment. In various embodiments, as illustrated, the respirator air outlet may be positioned external to the respirator housing 11 such that the respirator air outlet is not arranged within the internal respirator housing portion 12 defined by the one or more sidewalls of the respirator housing 11. For example, the respirator 10 may be configured such that the respirator air outlet (e.g., the blower assembly air outlet 113) may extend through a portion of the one or more sidewalls of the respirator housing 11.

In various embodiments, as the length of the respirator air flow path between the blower assembly air outlet and the respirator air outlet is decreased, the magnitude of the system errors caused by the configuration of the respirator air flow path downstream from the blower assembly air outlet is similarly minimized. For example, various errors that may correspond to a reduced operational efficiency and/or a dampened respirator production output may be introduced into the respirator system as a result of a back pressure within the respirator air flow path. For example, the back pressure may be realized at the blower assembly air outlet. In various embodiments, back pressure may be generated based at least in part on the length of a portion of the respirator air flow path downstream from the blower assembly air outlet (e.g., a blower scroll outlet). For example, the back pressure realized at the blower scroll air outlet may be directly proportional to the length of the respirator air flow path downstream therefrom. Further, the portion of the respirator air flow path downstream from the blower assembly air outlet (e.g., a blower scroll outlet) having one or more complex geometries, such as, for example, bends, curves, splits, and or the like, may similarly result in an increased back pressure realized at the blower assembly air outlet. Accordingly, in various embodiments, the respirator 10 may be configured such that the portion of the respirator air flow path extending between the blower assembly air outlet and the respirator air outlet may comprise a substantially minimized length and a substantially simplified geometry. For example, as illustrated in FIG. 6, the portion of the respirator air flow path downstream from the blower scroll air outlet is at least substantially minimized, as the respirator 10 is configured such that the respirator air outlet is defined by the blower assembly air outlet 113. Similarly, the geometry of the portion of the respirator air flow path downstream from the blower scroll air outlet, as illustrated, comprises an at least substantially simplified approximately linear configuration.

Figure 7:
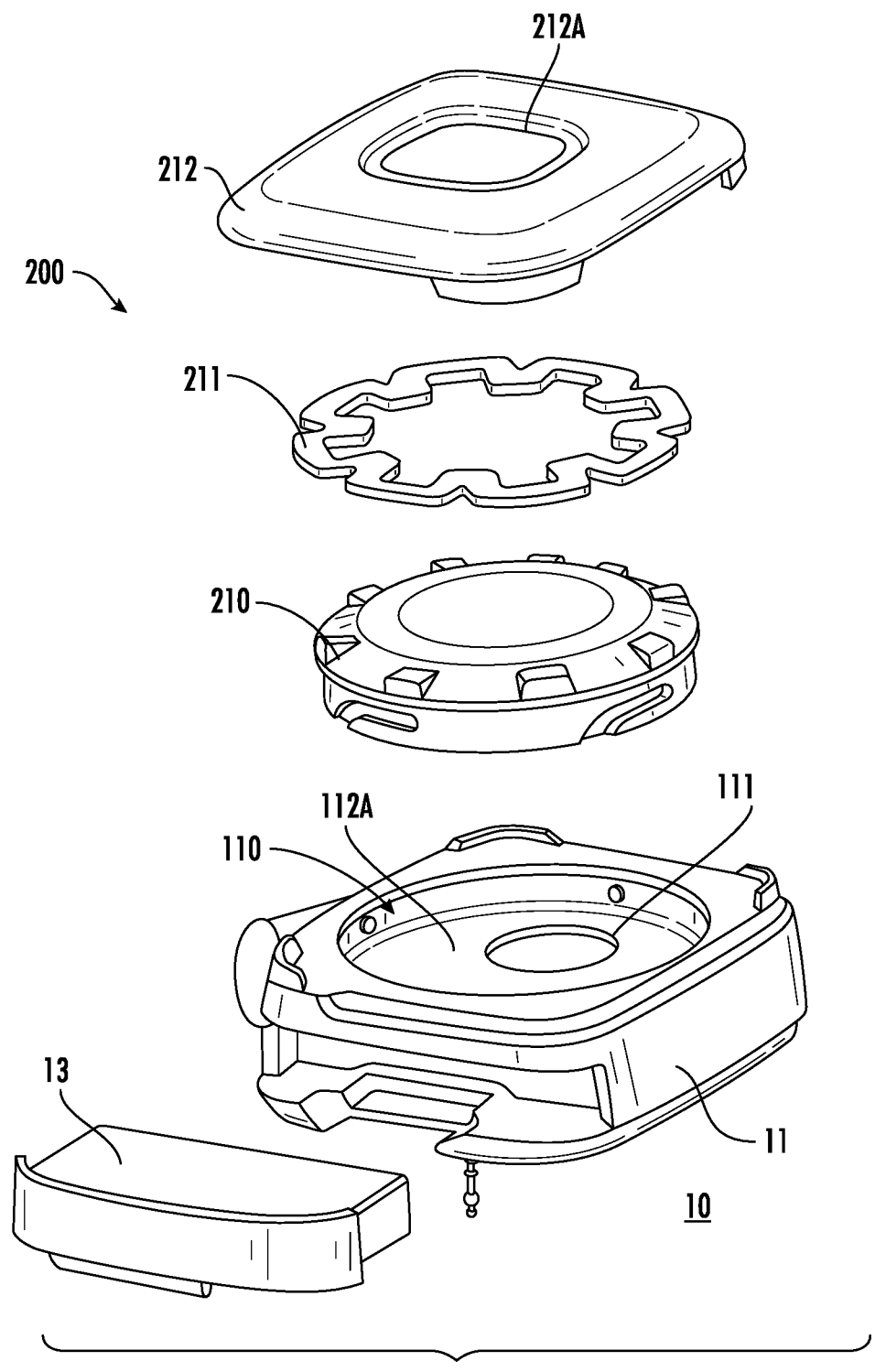
FIG. 7 illustrates an exploded perspective view of various components of an exemplary respirator apparatus in accordance with various embodiments.

FIG. 7 illustrates an exploded perspective view of various components of an exemplary respirator apparatus in accordance with various embodiments. In particular, FIG. 7 illustrates an exploded bottom perspective view of an exemplary filter assembly 200 arranged relative to a respirator housing 11 in accordance with various embodiments. In various embodiments, an exemplary respirator 10 described herein may further comprise a filter assembly 200 configured to extract various contaminants from within a volume of air received from an ambient environment by the respirator 10. For example, the filter assembly 200 may be configured to at least partially purify the volume of air prior to the volume of air being dispensed into a controlled environment. In various embodiments, the filter assembly 200 may comprise a filter element 210, a filter assembly arrangement component 211, and a filter element cover 212.

In various embodiments, the filter assembly 200 may comprise a filter element 210 configured to capture various contaminates such as, for example, particulate matter, airborne bacteria, and/or the like, from the volume of air traveling along the respirator air flow path. As a non-limiting example, in various embodiments, the filter element 210 may comprise one or both of a physical filter media and a chemical filter media. In various embodiments, the filter media of the filter element 210 may be configured based at least in part on a particular contaminant and/or type of contaminant that is sought to be extracted from the volume of ambient air traveling along the filter assembly air flow path. As described herein, the filter element 210 may be positioned upstream from a respirator air outlet such that the contaminants present within the volume of ambient air received by the respirator are extracted prior to the volume of air being dispensed into a controlled environment. Such an exemplary configuration may minimize the amount of contaminant within the purified air of the controlled environment. As described herein, purified air may be dispensed from a respirator air outlet at an output flowrate. As described herein, in various embodiments, the filter element 210 may define a portion of a respirator air flow path. Further, in various embodiments, the filter element 210 may comprise one or both of a filter assembly air inlet and a filter assembly air outlet.

In various embodiments, the filter assembly 200 may further comprise one or more filter assembly arrangement components 211. For example, as illustrated, a filter assembly arrangement component 211 may be positioned in between the filter element 210 and an internal surface of the filter element cover 212. Alternatively, or additionally, in various embodiments, a filter assembly arrangement component 211 may be positioned in between the filter element 210 and an outer blower base surface 112A so as to ensure that the filter element 210 and the outer blower base surface 112A are appropriately aligned and/or sufficiently spaced relative to one another such that a volume of air dispensed from the filter element 210 may travel to a blower assembly air inlet 111 positioned downstream therefrom. For example, the filter assembly arrangement component 211 may be configured to at least partially constrain the movement of one or more components of the filter assembly 200 (e.g., the filter element 210, the filter element cover 212) so as to ensure that the filter element 210 and the filter element cover 212 are appropriately aligned and sufficiently spaced relative to one another so as to define at least a portion of a filter assembly air flow path along which a volume of air may travel to a filter element 210.

In various embodiments, the filter element cover 212 may be configured to engage a portion of the respirator housing 11 such that the filter element cover 212 may be removably attached thereto. In various embodiments, the filter element cover 212 may be configured to at least partially cover the filter element 210 arranged within an internal respirator housing portion 12 so as secure the filter element 210 within the internal respirator housing portion 12 and/or to protect the filter element 210 from unwarranted physical engagement therewith by one or more forces within an ambient environment. In various embodiments, the filter element cover 212 may comprise an orifice 212A extending therethrough that may be configured to receive a volume of air from an ambient environment. The orifice 212A of the filter cover 212 may be configured such that the filter assembly 200 (e.g., the filter element 210) may receive a volume of air from an ambient environment in an exemplary circumstance wherein the filter element cover 212 is attached to the respirator housing 11. For example, in an exemplary circumstance wherein the filter assembly 200 comprises a filter element cover 212, the orifice 212A of the filter element cover 212 may define the filter assembly air inlet.

In various embodiments, the filter assembly 200 may comprise a filter assembly air inlet and a filter assembly air outlet. Further, in various embodiments, the filter assembly 200 may define a filter assembly air flow path extending between the filter air inlet and the filter air outlet along which the volume of air received by the filter assembly 200 may travel. In various embodiments, the filter assembly air flow path may define a portion of the respirator air flow path such that a volume of air traveling from the respirator air inlet and along the respirator air flow path may pass through at least a portion of the filter assembly 200. For example, the filter assembly air flow path may define a portion of the respirator air flow path positioned downstream from the filter assembly air inlet and upstream from the filter assembly air outlet. In various embodiments, for example, wherein the filter assembly comprises a filter element cover 212, the filter assembly air inlet may be defined by the orifice 212A extending through the filter element cover 212. Alternatively, in various embodiments wherein a filter element cover 212 is not included in the filter assembly, the filter assembly air inlet may be defined by one or more air intake portions of the filter element 210. In various embodiments, the filter assembly air outlet may be defined by one or more air outlet portions of the filter element 210. As described herein, purified air may be dispensed from the respirator air outlet at an output flowrate.

In various embodiments, the respirator 10 may be configured such that the filter assembly 200 may be housed in an external housing compartment defined by an exterior portion of the respirator housing 11. For example, as illustrated in FIG. 7, the respirator housing 11 may be defined at least in part by the blower frame element 110, which may be configured to engage at least a portion of the one or more sidewalls of the respirator housing 11 so as to define an internal respirator housing portion, as described herein. In such an exemplary circumstance wherein the blower frame element 110 defines a portion of the respirator housing 11, the outer blower base surface 112A may define an external surface of the respirator housing 11. In various embodiments, the external housing compartment configured to receive the filter assembly 200 may be defined at least in part by the blower frame element 110 (e.g., the outer blower base surface 112. As described herein, the blower frame element 110 may define the blower assembly air inlet 111. For example, at least a portion of the filter assembly (e.g., the filter element 210) may be positioned within the external housing compartment defined by the blower frame element 110 such that the filter assembly air outlet defined by the filter element 210 may be fluidly connected (e.g., either directly or indirectly) to the blower assembly air inlet 111. In such an exemplary circumstance, the respirator 10 may be configured such that the filter assembly 200 is positioned upstream from the blower assembly, as measured along the respirator air flow path, between the respirator air inlet and the blower assembly air outlet. Alternatively, in various embodiments, the respirator 10 may be configured such that the filter assembly 200 is positioned downstream from the blower assembly, along the respirator air flow path between the blower assembly air outlet and the respirator air outlet.

In various embodiment, as illustrated in FIG. 7, the respirator housing 11 may be further configured to house a removeable power source 13, such as, for example, a battery, configured to supply power to one or more electrical components of the respirator 10 so as to facilitate the mobility of the respirator 10. In various embodiments, the removeable power source 13 may comprise a rechargeable battery cartridge and/or one or more replaceable batteries.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A respirator apparatus comprising:
   a respirator housing comprising an outer casing defining an exterior portion of the respirator apparatus; and
   a compact blower assembly comprising:
      an impeller configured to pull a volume of air into the blower assembly through a blower assembly air inlet;
      a blower scroll configured to receive the volume of air at a blower scroll air inlet and direct the volume of air toward a blower scroll air outlet, the blower scroll comprising:
         a first blower scroll component comprising at least a portion of a blower frame element and defining the blower scroll air inlet, wherein the blower frame element comprises a portion of the respirator housing; and
         a second blower scroll component comprising a scroll cover secured to the blower frame element so as to define an internal scroll flow chamber comprising a cavity positioned between the scroll cover and the portion of the blower frame element corresponding to the first blower scroll component;
      wherein the blower scroll is configured to house the impeller within the internal scroll flow chamber;
      wherein the blower scroll air inlet embodies the blower assembly air inlet;
   wherein the scroll cover comprises an external back surface having an at least substantially planar configuration, the external back surface defining a portion of an exterior of the scroll cover that is configured to engage at least a portion of a printed control board assembly.

2. The respirator apparatus of claim 1, wherein a thickness of the blower frame element extends between a first blower frame element surface and a second blower frame element surface, wherein the first blower frame element surface is configured to receive an interface portion of the scroll cover such that the scroll cover may be secured thereto, wherein the internal scroll flow chamber is defined between the scroll cover and the first blower frame element surface.

3. The respirator apparatus of claim 2, wherein the first blower frame element surface comprises one or more geometric features configured to facilitate an airflow of the volume of air from the blower scroll air inlet to the blower scroll air outlet within the internal scroll flow chamber.

4. The respirator apparatus of claim 2, wherein the impeller is secured to the first blower frame element surface.

5. The respirator apparatus of claim 1, wherein the scroll cover comprises an interface surface configured to engage a first blower frame element surface so as to define an interface between the first blower scroll component and the second blower scroll component, the interface surface having a substantially annular configuration defined in part by an outer perimeter of the scroll cover, wherein the interface between the first blower scroll component and the second blower scroll component comprises an interface perimeter corresponding to the interface surface of the scroll cover.

6. The respirator apparatus of claim 5, wherein the blower scroll is configured such that the interface perimeter extends along the first blower frame element surface so as to at least substantially surround the blower scroll air inlet.

7. The respirator apparatus of claim 1, further comprising a blower motor configured to drive a rotation of the impeller within the internal scroll flow chamber and the printed control board assembly, the printed control board assembly comprising:
   motor control circuitry configured to facilitate transmission of one or more signals to the blower motor; and
   respirator control circuitry configured to facilitate transmission of one or more signals to one or more respirator operational components.

8. The respirator apparatus of claim 1, wherein the scroll cover further comprises a beeper interface element integrated into an exterior of the scroll cover and configured to be in electronic communication with the printed control board assembly and a beeper element so as to enable an alert functionality corresponding to one or more predetermined blower assembly operating parameters.

9. The respirator apparatus of claim 1, further comprising a filter assembly configured to at least partially purify the volume of air, wherein the filter assembly defines a portion of a respirator air flow path arranged upstream from the blower assembly.

10. The respirator apparatus of claim 9, wherein the respirator housing comprises:
an internal respirator housing portion defined at least in part by one or more sidewalls; and
an external housing compartment disposed about an exterior of the respirator housing and defined at least in part by an outer surface of the blower frame element;
wherein the blower assembly is disposed within the internal respirator housing portion and the filter assembly is disposed within the external housing compartment.

11. A compact blower assembly comprising:
an impeller configured to pull a volume of air into the blower assembly through a blower assembly air inlet;
a blower scroll configured to receive the volume of air at a blower scroll air inlet and direct the volume of air toward a blower scroll air outlet, the blower scroll comprising:
a first blower scroll component comprising at least a portion of a blower frame element and defining the blower scroll air inlet, wherein the blower frame element is configured so as to define at least a portion of an exterior of the blower assembly;
a second blower scroll component comprising a scroll cover secured to the blower frame element so as to define an internal scroll flow chamber, wherein the internal scroll flow chamber comprises a cavity positioned between the scroll cover and the portion of the blower frame element corresponding to the first blower scroll component; and
wherein the blower scroll is configured to house the impeller within the internal scroll flow chamber;
wherein the blower scroll air inlet comprises an opening extending through a thickness of the blower frame element, wherein the blower assembly is configured such that the blower scroll air inlet embodies the blower assembly air inlet; and
wherein the scroll cover comprises an external back surface having an at least substantially planar configuration, the external back surface defining a portion of an exterior of the scroll cover that is configured to engage at least a portion of a printed control board assembly.

12. The compact blower assembly of claim 11, wherein the thickness of the blower frame element extends between a first blower frame element surface and a second blower frame element surface, wherein the first blower frame element surface is configured to receive an interface portion of the scroll cover such that the scroll cover may be secured thereto, wherein the internal scroll flow chamber is defined between the scroll cover and the first blower frame element surface.

13. The compact blower assembly of claim 12, wherein the first blower frame element surface comprises one or more geometric features configured to facilitate an airflow of the volume of air from the blower scroll air inlet to the blower scroll air outlet within the internal scroll flow chamber.

14. The compact blower assembly of claim 12, wherein the impeller is secured to the first blower frame element surface.

15. The compact blower assembly of claim 11, wherein the scroll cover comprises an interface surface configured to engage a first blower frame element surface so as to define an interface between the first blower scroll component and the second blower scroll component, the interface surface having a substantially annular configuration defined in part by an outer perimeter of the scroll cover, wherein the interface between the first blower scroll component and the second blower scroll component comprises an interface perimeter corresponding to the interface surface of the scroll cover.

16. The compact blower assembly of claim 15, wherein the blower scroll is configured such that the interface perimeter extends along the first blower frame element surface so as to at least substantially surround the blower scroll air inlet.

17. The compact blower assembly of claim 11, further comprising a blower motor configured to drive a rotation of the impeller within the internal scroll flow chamber and the printed control board assembly, the printed control board assembly comprising:
motor control circuitry configured to facilitate transmission of one or more signals to the blower motor; and
respirator control circuitry configured to facilitate transmission of one or more signals to one or more respirator operational components.

18. The compact blower assembly of claim 11, wherein the scroll cover further comprises a beeper interface element integrated into an exterior of the scroll cover and configured to be in electronic communication with the printed control board assembly and a beeper element so as to enable an alert functionality corresponding to one or more predetermined blower assembly operating parameters.

* * * * *